US00PP24220P3

(12) United States Plant Patent
Olesen

(10) Patent No.: US PP24,220 P3
(45) Date of Patent: Feb. 11, 2014

(54) CLIMBING ROSE PLANT NAMED 'POULCY026'

(50) Latin Name: ***Rosa* hybrid**
Varietal Denomination: Poulcy026

(75) Inventor: Mogens Nyegaard Olesen, Fredensborg (DK)

(73) Assignee: Poulsen Roser A/S, Freedensborg (DK)

( * ) Notice: Subject to any disclaimer, the term of this patent is extended or adjusted under 35 U.S.C. 154(b) by 34 days.

(21) Appl. No.: 13/507,030

(22) Filed: May 31, 2012

(65) Prior Publication Data

US 2013/0326741 P1 Dec. 5, 2013

(51) Int. Cl.
*A01H 5/00* (2006.01)

(52) U.S. Cl.
USPC ..... Plt./111

(58) Field of Classification Search
USPC ..... Plt./111
See application file for complete search history.

*Primary Examiner* — Kent L Bell

(57) ABSTRACT

A new garden rose plant of the climbing class which has abundant, yellow flowers and attractive foliage. This new and distinct variety has shown to be uniform and stable in the resulting generations from asexual propagation.

1 Drawing Sheet

Botanical designation: *Rosa* hybrid.
Variety denomination: 'Poulcy026'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2004 and the resulting seeds were planted in a controlled environment in Fredensborg, Denmark. The new variety, named 'Poulcy026', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Exceptional disease resistance.
4. Reduced apical dominance in flowering habit. The new variety consistently branches and produces flowers evenly from the lower branches to the top of the plant.

This combination of qualities is not present in previously available commercial cultivars of this type, known to the inventor, and distinguish 'Poulcy026' from all other varieties of which we are aware.

As part of the rose development program, Mogens N. Olesen germinated the seeds from the aforementioned hybridization during winter of 2004 and conducted evaluations on the resulting seedlings in a controlled environment in Fredensborg, Denmark. 'Poulcy026' was selected in the spring of 2005 by the inventor as a single plant from the progeny of the aforementioned hybridization.

Asexual reproduction of 'Poulcy026' by traditional budding and rooted cuttings was first done by Mogens N. Olesen in the nursery in Fredensborg, Denmark in July, 2005. This initial and other subsequent asexual propagations conducted in controlled environments have demonstrated that the characteristics of 'Poulcy026' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulcy026'. Specifically illustrated in the drawing are flowers at various stages of development, flower in parts, leaves, and stems.

DETAILED DESCRIPTION OF THE VARIETY

The following is a description of 'Poulcy026', as observed in its growth in a field nursery in Bakersfield, Calif. Observed plants are 2 years of age, and were grown on their own roots. Color references are made using The Royal Horticultural Society (London, England) Colour Chart, 2001, except where common terms of color are used.

Several physical characteristics of a non-patented rose variety 'Poulhult' are compared to 'Poulcy026' in Chart 1.

CHART 1

| | 'Poulcy026' | 'Poulhult' |
|---|---|---|
| Petal Count | 16 | 18 to 20 |
| Flower Diameter | 70 mm | 55 to 60 mm |
| General Tonality of Flower Color | Yellow Group 10B. | Yellow-Orange 14C |

Flower and Flower Bud

Blooming habit: Continuous.
Flower bud:

*Size*.—Upon opening, 23 mm in length from base of receptacle to end of bud. Bud diameter is 10 mm.

*Bud form*.—Ovoid.
*Bud color*.—As sepals divide petals are Yellow-Orange Group 15A.
*Sepal inner surface*.—Color: Yellow-Green Group 144C. Surface: Smooth.
*Sepal outer surface*.—Color: Yellow-Green Group 144A. Texture: Smooth.
*Sepal shape*.—Apex: Cirrhose. Base: Flat at union with receptacle.
*Sepal margin*.—Margins have weak foliaceous appendages on three of the five sepals.
*Sepal size*.—30 mm long by 7 mm wide.
*Receptacle*.—Texture: Smooth. Size: 8 mm in height by 5 mm wide. Color: Yellow-Green Group 144A. Shape: Elliptical.
*Pedicel*.—Surface: Somewhat rough with many stipitate glands. Length: Average 40 mm. Diameter: 2 mm on average. Color: Yellow-Green Group 144A. Strength: Moderate.

Flower bud development: Flower buds are borne in clusters of 3 to 5 flower buds per stem, resembling a corymb. Reduced apical dominance in flower habit causes flower buds to develop evenly from the base of the plant to the upper branches.

Flower bloom:
*Fragrance*.—Light fruity scent.
*Duration*.—The blooms have a duration on the plant of approximately 10 to 14 days. Petals fall cleanly away from plant after flowers have fully matured.
*Size*.—Flower diameter is 70 mm when open. Flower depth is 30 mm.
*Flower shape*.—General shape is an open cup with petals that curve out from the center.
*Shape of flower, side view*.—The upper portion is flat. The lower portion is concave.

Petalage: Under normal conditions, flowers have 16 petals total, 3 of which are petaloids.

General tonality of flower: Open flowers are Yellow Group 10B.

Petal color:
*Upon opening, outer and inner petals*.—Upper surface: Yellow Group 12A. Lower surface: Yellow-Orange Group 15B.
*Basal petal spots*.—No distinctive coloration at the petal base observed.
*After opening, outer and inner petals*.—Upper surface: Yellow Group 10B. Lower surface: Yellow Group 10C.
*Basal petal spots*.—No distinctive coloration.

Petals:
*Petal reflex*.—Somewhat reflexed.
*Margin*.—Entire and uniform. Weak undulations of margin observed.
*Shape*.—Generally narrow elliptic. Apex shape: Rounded. Base shape: Acute.
*Size*.—35 mm (l)×30 mm (w).
*Texture*.—Smooth.
*Thickness*.—Average.

Petaloids:
*Size*.—20 mm (l) by 5 mm (w).
*Quantity*.—About 3.
*Shape*.—Apex and base are acute.
*Color*.—Yellow Group 10B.

Reproductive parts:
*Pollen*.—None observed.
*Anthers*.—Size: 2 mm in length. Color: Greyed-Orange Group N163B. Quantity: 65 on average.
*Filaments*.—Color: Yellow Group 13A. Length: 7 to 10 mm.
*Pistils*.—Length: 4 mm. Quantity: 35 on average.
*Stigmas*.—Color: Yellow-Green Group 151D.
*Styles*.—Color: Yellow-Green Group 151D.
*Location of stigmas*.—Tightly clustered at the center, while filaments are open and extended outward.
*Hips*.—None Observed.

Plant

Plant growth: Arching. Plants are 75 cm in height, and 75 cm wide.

Stems:
*Color*.—Juvenile growth: Yellow-Green Group 144B. Mature growth: Yellow-Green Group 144B.
*Length*.—On average, canes are 35 cm from the base of the plant to the flowering portion.
*Diameter*.—4 mm.
*Internodes*.—On mature canes, there is an average distance of 40 mm between nodes.
*Surface texture*.—Young wood: Smooth. Older wood: Smooth.

Long prickles:
*Incidence*.—4 prickles per 10 cm of stem.
*Size*.—Average length of prickles on mature stems is 10 mm.
*Shape*.—Upper portion is linear. Lower portion is linear.
*Color*.—Juvenile prickles: Greyed-Yellow Group 160B. Mature prickles: Greyed-Yellow Group 160B.

Plant foliage:
*Compound leaf*.—100 mm (l)×60 (w).
*Quantity*.—2 leaves per 10 cm of stem on average.
*Leaf bearing angle to the stem*.—90 degrees.
*Color of juvenile foliage*.—Upper side: Yellow-Green Group 144B. Lower side: Yellow-Green Group 144B. Anthocyanin: Greyed-Orange Group 173A generalized on lower side.
*Color of mature foliage*.—Upper side: Yellow-Green Group 146A. Lower side: Yellow-Green Group 146B.

Plant leaves and leaflets:
*Stipules*.—Size: 10 mm in length. Quantity: 2 per compound leaf. Shape: Linear, slightly broad based with outward extending apices. Margins: Finely serrated. Color: Yellow-Green Group 144A.
*Petiole*.—Length: 10 mm. Diameter: 2 mm.
*Upper surface*.—Color: Yellow-Green Group 144A.
*Lower surface*.—Color: Yellow-Green Group 144B.
*Rachis*.—Length: 35 mm.
*Upper surface*.—Color: Yellow-Green Group 144A.
*Lower surface*.—Color: Yellow-Green Group 144B.
*Leaflet*.—Quantity: Normal number of leaflets per leaf in middle of the stem is 7 leaflets. Margins: Serrated. Size: Average size of the terminal leaflet on normal leaves is 35 mm in length by 28 mm wide. Shape: Generally ovate. Base: Rounded. Apex: Cuspidate. Texture: Smooth. Thickness: Average. Arrangement: Odd pinnate. Venation: Reticulate. Glossiness: Moderately glossy.

Disease resistance: Above average resistance to powdery and downy mildew, rust, black spot, and Botrytis under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Climbing rose class named 'Poulcy026', substantially as illustrated and described herein, due to its abundant yellow flowers, disease resistance, and extended period of bloom.

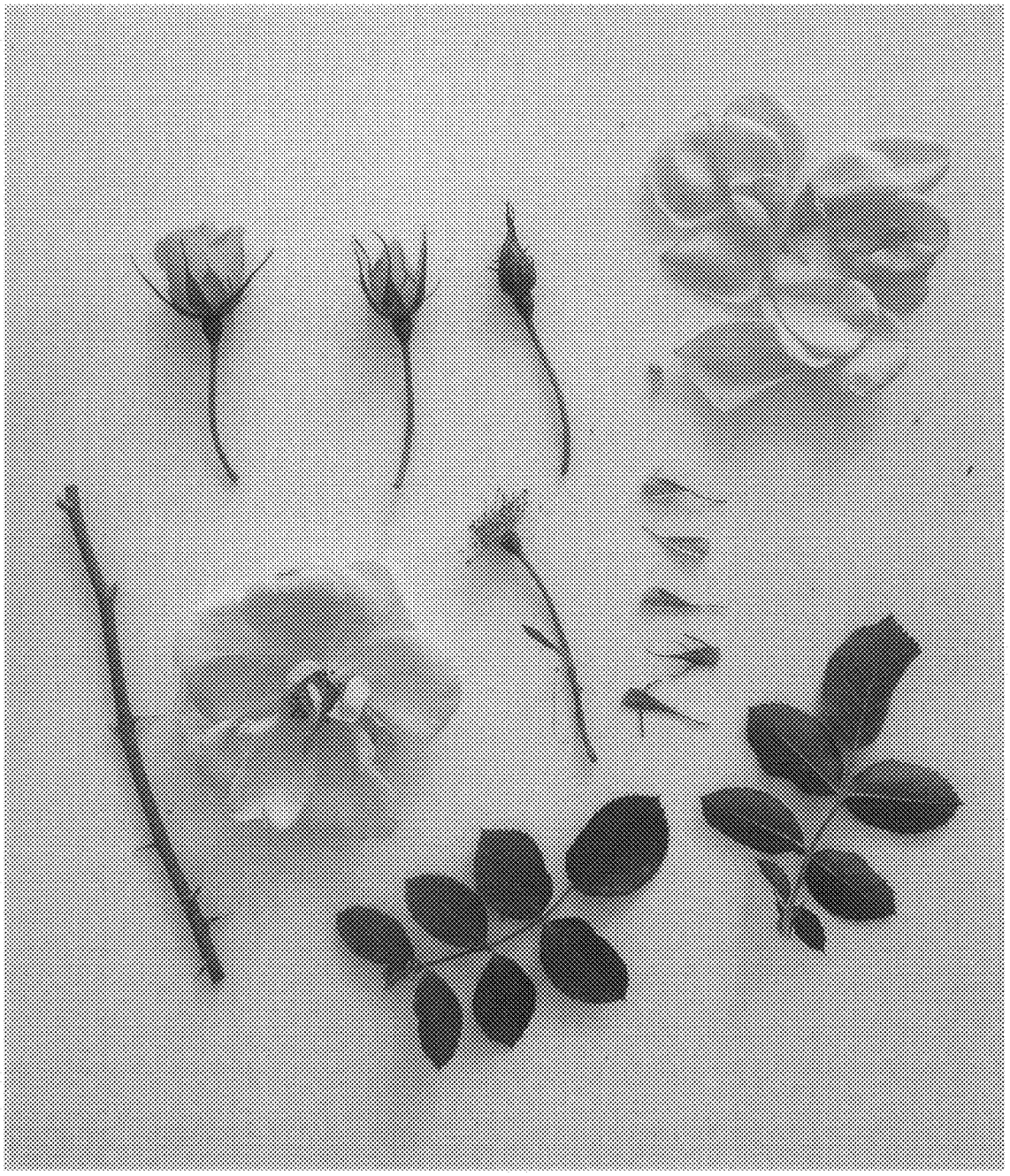

* * * * *